United States Patent
Carranza et al.

(10) Patent No.: US 8,779,123 B2
(45) Date of Patent: Jul. 15, 2014

(54) PROCESS FOR THE SYNTHESIS OF 3-(2-BROMO-4,5-DIMETHOXYPHENYL) PROPANENITRILE, AND APPLICATION IN THE SYNTHESIS OF IVABRADINE AND ADDITION SALTS THEREOF WITH A PHARMACEUTICALLY ACCEPTABLE ACID

(71) Applicant: Les Laboratoires Servier, Suresnes Cedex (FR)

(72) Inventors: Maria Del Pilar Carranza, Villarrubia De Los Ojos (ES); Maria Isabel Garcia Aranda, Toledo (ES); José Lorenzo Gonzalez, Toledo (ES); Frédéric Sanchez, Cobisa (ES)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 14/095,377

(22) Filed: Dec. 3, 2013

(65) Prior Publication Data

US 2014/0163220 A1    Jun. 12, 2014

(30) Foreign Application Priority Data

Dec. 6, 2012 (FR) ..................................... 12 61714

(51) Int. Cl.
C07D 223/16 (2006.01)
C07C 255/03 (2006.01)

(52) U.S. Cl.
USPC ......................................... 540/523; 558/410

(58) Field of Classification Search
USPC .......................................... 540/523; 558/410
See application file for complete search history.

(56) References Cited

U.S. PATENT DOCUMENTS

2002/0091273 A1    7/2002   Berger

OTHER PUBLICATIONS

Aisling, O'Byrne, et al., Organic and Biomolecular Chemistry, vol. 8, No. 3, p. 539-545, Jan. 1, 2010.
French Preliminary Serach Report for FR1261714 of Jul. 3, 2013.
Shuji Yamashita, et al., Journal of Organic Chemistry, vol. 76, No. 8, p. 2408-2425, Apr. 15, 2011.
Trost, et al., Chemistry—A European Journal, vol. 16, No. 32, p. 9772-9776, Aug. 23, 2010,—Trost "Supporting Information" Chemistry, A European Journal Jan. 1, 2010, p. SI 1-SI 31.
WF Barthel, Journal of Organic Chemistry, vol. 23, p. 1012-1014, Jan. 1, 1958.
Zhao Sheng Yin, et al., Journal of Chemical Research, No. 7, p. 420-422, Jan. 1, 2009.

*Primary Examiner* — Bruck Kifle
(74) *Attorney, Agent, or Firm* — Hueschen and Sage

(57) ABSTRACT

Process for the synthesis of the compound of formula (I):

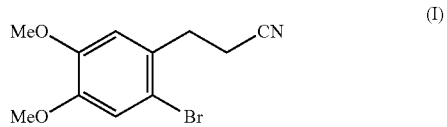

Application in the synthesis of ivabradine, addition salts thereof with a pharmaceutically acceptable acid and hydrates thereof.

7 Claims, No Drawings

PROCESS FOR THE SYNTHESIS OF 3-(2-BROMO-4,5-DIMETHOXYPHENYL) PROPANENITRILE, AND APPLICATION IN THE SYNTHESIS OF IVABRADINE AND ADDITION SALTS THEREOF WITH A PHARMACEUTICALLY ACCEPTABLE ACID

The present invention relates to a process for the synthesis of (3-(2-bromo-4,5-dimethoxyphenyl)propanenitrile of formula (I):

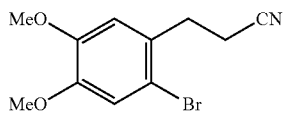

and to the application thereof in the synthesis of ivabradine and addition salts thereof with a pharmaceutically acceptable acid.

The compound of formula (I) obtained in accordance with the process of the invention is useful in the synthesis of ivabradine of formula (II):

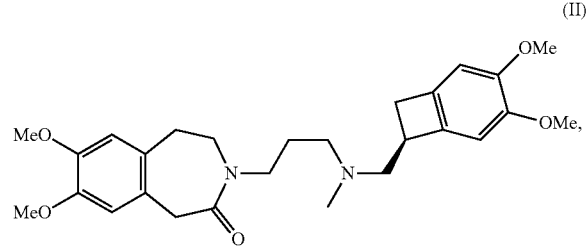 [SMILES: COc1cc2c(cc1OC)CC(=O)N(CCCN(C)C[C@H]1Cc3cc(OC)c(OC)cc31)CC2]

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
which may be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarction and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859.

That patent specification describes the preparation of ivabradine starting from 3,4-dimethoxybicyclo[4.2.0]octa-1,3,5-triene-7-carbonitrile of formula (III):

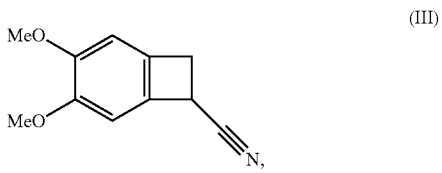 [SMILES: COc1cc2c(cc1OC)C(C#N)C2]

which is converted into the compound of formula (IV):

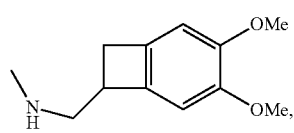

which is resolved to yield the compound of formula (V):

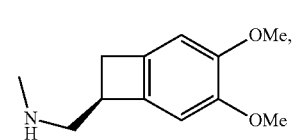

which is reacted with the compound of formula (VI):

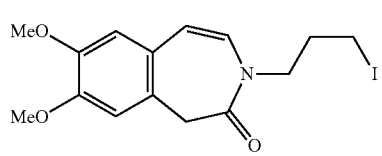

to yield the compound of formula (VII):

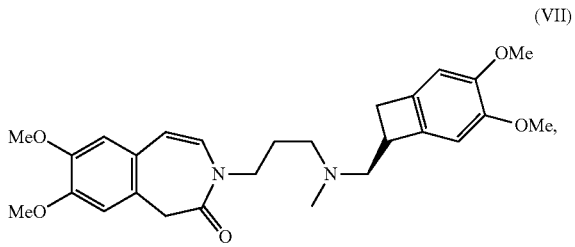

the catalytic hydrogenation of which yields ivabradine, which is then converted into its hydrochloride.

The preparation of the compound of formula (III) starting from the compound of formula (I) is described in *Tetrahedron* 1973, 29, pp 73-76.

That same document also describes a synthesis route for the compound of formula (I), starting from 2-bromo-4,5-dimethoxybenzaldehyde, in three steps in an overall yield of 65%.

More recently, Zhao et al. have described synthesis of the compound of formula (I), starting from 3,4-dimethoxybenzaldehyde, in three steps in an overall yield of 51% (CN 101 407 474 A and *J. Chem. Res.* 2009, 7, pp 420-422).

The compound of formula (I) is a key intermediate in the synthesis of ivabradine.

In view of the industrial value of ivabradine and its salts, it has been imperative to find an effective process allowing (3-(2-bromo-4,5-dimethoxyphenyl)propanenitrile of formula (I) to be obtained in an excellent yield.

The present invention relates to a process for the synthesis of the compound of formula (I):

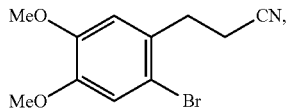

characterised in that the compound of formula (VIII):

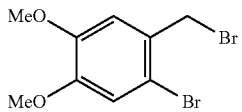

is subjected to the action of a base in the presence of acetonitrile in an organic solvent to yield the compound of formula (I).

Among the bases that may be used to carry out the conversion of the compound of formula (VIII) into the compound of formula (I), there may be mentioned, without implying any limitation, n-butyllithium, lithium diisopropylamide, potassium bis(trimethylsilyl)amide, potassium tert-butoxide and potassium hydroxide.

The base preferably used to carry out the conversion of the compound of formula (VIII) into the compound of formula (I) is n-butyllithium.

Among the solvents that may be used to carry out the conversion of the compound of formula (VIII) into the compound of formula (I), there may be mentioned, without implying any limitation, tetrahydrofuran and acetonitrile.

The solvent preferably used to carry out the conversion of the compound of formula (VIII) into the compound of formula (I) is tetrahydrofuran.

The conversion of the compound of formula (VIII) into the compound of formula (I) is carried out at a temperature preferably between −65° C. and 25° C., inclusive.

The present invention relates also to a process for the synthesis of the compound of formula (I) starting from the compound of formula (VIII), characterised in that said compound of formula (VIII) is prepared starting from the compound of formula (IX):

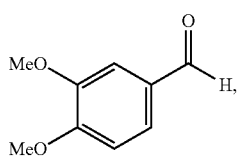

which is converted, by a reduction reaction, into the compound of formula (X):

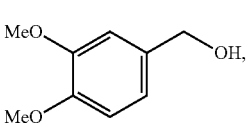

which is converted, by a bromination reaction, into the compound of formula (VIII):

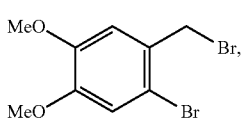

which is converted into the product of formula (I):

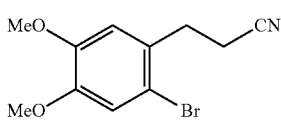

in accordance with the process described hereinabove.

The reduction reaction performed on the compound of formula (IX) may be carried out under the conditions described in the publication *Org. Biomol. Chem.* 2010, 8, 539-545.

The bromination reaction performed on the compound of formula (X) may be carried out under the conditions described in the publication *Chem. Eur. J.* 2010, 16, 9772-9776.

The present invention relates also to a process for the synthesis of ivabradine starting from the compound of formula (I) prepared in accordance with the process of the invention and converted into the compound of formula (III) following the teaching of the prior art (*Tetrahedron* 1973, 29, pp 73-76) by an intramolecular cyclisation reaction in a basic medium, said compound of formula (III) then being converted into ivabradine in accordance with the process described in EP 0 534 859.

The Examples that follow illustrate the invention.

The melting point was measured using a BÜCHI B-545 Melting Point Apparatus (Volt. 230VAC, Freq. 50/60 Hz, Power max. 220W).

LIST OF ABBREVIATIONS USED m.p.: melting point
THF: tetrahydrofuran

Preparation 1: (3,4-dimethoxyphenyl)methanol

Based on *Org. Biomol. Chem.* 2010, 8, 539-545

10 g (60.2 mmoles, 1 eq.) of 3,4-dimethoxybenzaldehyde are dissolved in 300 mL of methanol and the solution is cooled to 0° C. 2.73 g (72.2 mmoles, 1.2 eq.) of NaBH₄ are added in portions and the reaction mixture is stirred for 20 minutes and then hydrolysed using 10 mL of 1M aqueous HCl solution until the medium is at neutral pH. The solvent is removed under reduced pressure and the residue is extracted using 3×50 mL of dichloromethane. The organic phases are combined, dried over MgSO$_4$, filtered and concentrated under reduced pressure to yield 9.88 g of a clear oil.
Yield=98%

Preparation 2:
1-bromo-2-(bromomethyl)-4,5-dimethoxybenzene

Based on *Chem. Eur. J.* 2010, 16, 9772-9776
To a solution of (3,4-dimethoxyphenyl)methanol (101.5 mmoles, 14.85 mL, 1 eq.) in 80 mL of glacial acetic acid there are added, at 0° C., over 30 minutes, 6 mL of dibromine (116.8 mmoles, 1.15 eq.) in 18 mL of glacial acetic acid. The reaction mixture is stirred for 3 hours and then brought back to ambient temperature. Stirring is stopped in order to allow the 1-bromo-2-(bromomethyl)-4,5-dimethoxybenzene to precipitate completely overnight. The precipitate is filtered off, washed with methanol and recrystallised from methanol to yield 29.9 g of a light-yellow powder.
Yield=95%

Example 1

3-(2-bromo-4,5-dimethoxyphenyl)propanenitrile

To a solution of 0.3 mL of acetonitrile (5.8 mmoles, 1.8 eq.) in 15 mL of THF there are added, at −60° C., 1.77 mL of n-butyllithium (2M in cyclohexane, 3.5 mmoles, 1.1 eq.). The solution is stirred for 15 minutes at −60° C. and then 1 g of 1-bromo-2-(bromomethyl)-4,5-dimethoxybenzene (3.2 mmoles) dissolved in 5 mL of THF is added. The reaction mixture is stirred for 1 hour and then hydrolysed using 10 mL of water and extracted twice with ethyl acetate. The organic phases are combined and evaporated under reduced pressure. The crude reaction product is purified by chromatography on silica gel (eluant: methylcyclohexane/ethyl acetate (70/30)). After evaporating off the solvent under reduced pressure, 505 mg of an orange oil which crystallises in the form of a beige solid are obtained.
Yield=58%
m.p.=74-81° C.

Example 2

3,4-dimethoxybicyclo[4.2.0]octa-1,3,5-triene-7-carbonitrile

Based on *Tetrahedron* 1973, 29, pp 73-76
To a solution of NaNH$_2$, prepared starting from 200 mL of liquid NH$_3$ and 1 g of Na (catalyst: FeCl$_3$) there are added, in portions, 5.4 g of 3-(2-bromo-4,5-dimethoxyphenyl)propanenitrile and the reaction mixture is stirred at ambient temperature for 2 hours. After evaporating off the excess NH$_3$, 2 g of NH$_4$Cl and 200 mL of water are added in portions. The grey crystals formed are collected and recrystallised from ethanol to yield 2.38 g of the expected product.
Yield=74%
m.p.=84-85° C.

Example 3

3,4-dimethoxy-N-methylbicyclo[4.2.0]octa-1,3,5-trien-7-amine

Based on EP 0 534 859

Step 1: 3,4-dimethoxybicyclo[4.2.0]octa-1,3,5-trien-7-amine hydrochloride 312 mL of a molar solution of borane complexed with THF are added dropwise, and whilst stiffing at ambient temperature, to a solution of 25 g of 3,4-dimethoxybicyclo[4.2.0]octa-1,3,5-triene-7-carbonitrile in 250 mL of THF and left in contact for 12 hours; 200 mL of ethanol are then added and stirring is carried out for 1 hour. 100 mL of 3.3N ethereal HCl are added dropwise. 27.7 g of the expected product are obtained.
Yield=90%
m.p.=205° C.

Step 2: ethyl (3,4-dimethoxybicyclo[4.2.0]octa-1,3,5-trien-7-yl)carbamate 1.5 mL of ethyl chloroformate are poured into a suspension of 3.4 g of the compound obtained in Step 1 in 4.5 mL of triethylamine and 50 mL of dichloromethane and left overnight, whilst stiffing at ambient temperature; washing with water and with 1N hydrochloric acid is then carried out. Drying is carried out and the solvent is evaporated off to dryness. 3.2 g of an oil corresponding to the expected product are obtained.
Yield=80%

Step 3: 3,4-dimethoxy-N-methylbicyclo[4.2.0]octa-1,3,5-trien-7-amine 3.2 g of the compound obtained in Step 2 dissolved in 30 mL of THF are added to a suspension of 0.9 g of LiAlH$_4$ in 20 mL of THF. Refluxing is carried out for 1 hour 30 minutes, then hydrolysing using 0.6 ml of water and 0.5 mL of 20% sodium hydroxide solution and, finally, 2.3 mL of water. The mineral salts are then filtered off, rinsed with THF and then the filtrate obtained is evaporated to dryness. 2.3 g of the expected compound are obtained.
Yield=92%

Example 4

(7S)-3,4-dimethoxy-N-methylbicyclo[4.2.0]octa-1,3,5-trien-7-amine

Based on EP 0 534 859
The amine obtained in Example 3 is reacted with an equimolar amount of (d) camphorsulphonic acid in ethanol. After evaporating off the solvent in vacuo, the salt is recrystallised first from ethyl acetate and then from acetonitrile until the target enantiomer is obtained with an optical purity of more than 99% (evaluated by HPLC on a Chiralcel® OD column).

Example 5

3-{3-[{[(7S)-3,4-dimethoxybicyclo[4.2.0]octa-1,3,5-trien-7-yl]methyl}-(methyl)amino]propyl}-7,8-dimethoxy-1,3-dihydro-2H-3-benzazepin-2-one Based on EP 0 534 859
A solution of the (d) camphorsulphonate salt obtained in Example 4 in ethyl acetate is brought to basic pH using sodium hydroxide and then the organic phase is separated off, washed, dried over Na$_2$SO$_4$ and evaporated.
A mixture composed of 5.6 g of potassium carbonate, 2.2 g of the above amine in 100 mL of acetone and 4 g of 3-(3-iodopropyl)-7,8-dimethoxy-1,3-dihydro-2H-3-benzazepin-2-one is then refluxed for 18 hours.
The solvent is evaporated off in vacuo, and the residue is taken up in ethyl acetate and then extracted with 3N hydrochloric acid.

The aqueous phase separated off is brought to basic pH using sodium hydroxide and is then extracted with ethyl acetate. After washing until neutral and drying over MgSO₄, evaporation in vacuo is carried out to obtain 4.5 g of an oil which is purified on a silica column using a mixture of dichloromethane/methanol (90/10) as eluant.

Yield=64%

Example 6

3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzazepin-2-one Based on EP 0 534 859

5 g of the compound obtained in Example 5 in 50 mL of glacial acetic acid are hydrogenated in a Parr apparatus under a hydrogen pressure of 4.9 bar at ambient temperature for 24 hours in the presence of 1 g of palladium hydroxide 10%. The catalyst is filtered off, the solvent is evaporated off, and then the dry residue is taken up in water and ethyl acetate. The organic phase is dried over anhydrous magnesium sulphate, concentration in vacuo is carried out and then the residue is purified on a silica column using a mixture of dichloromethane/methanol (95/5) as eluant.

After recrystallisation from ethyl acetate, 2 g of the expected compound are obtained.

Yield=40% m.p.=101-103° C.

The invention claimed is:

1. A Process for the synthesis of a compound of formula (I):

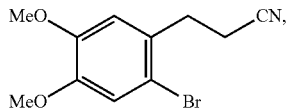

(I)

wherein the compound of formula (VIII):

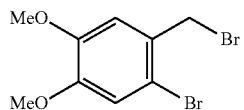

(VIII)

is subjected to the action of a base in the presence of acetonitrile in an organic solvent to yield the compound of formula (I).

2. The process according to claim 1, wherein the base used to carry out the conversion of the compound of formula (VIII) into the compound of formula (I) is selected from n-butyllithium, lithium diisopropylamide, potassium bis(trimethylsilyl)amide, potassium tert-butoxide and potassium hydroxide.

3. The process according to claim 2, wherein the base used to carry out the conversion of the compound of formula (VIII) into the compound of formula (I) is n-butyllithium.

4. The process according to claim 1, wherein the organic solvent used to carry out the conversion of the compound of formula (VIII) into the compound of formula (I) is tetrahydrofuran.

5. The process according to claim 1, wherein the conversion of the compound of formula (VIII) into the compound of formula (I) is carried out at a temperature between −65° C. and 25° C., inclusive.

6. The process according to claim 1, wherein the compound of formula (VIII) is prepared starting from a compound of formula (IX):

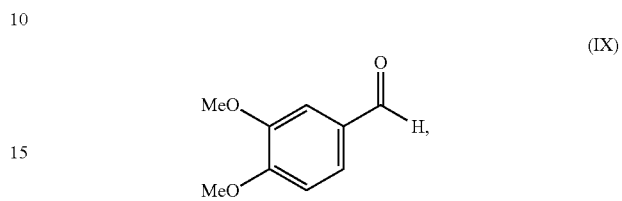

(IX)

which is converted, by a reduction reaction, into a compound of formula (X):

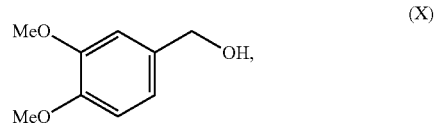 [SMILES: COc1ccc(CO)cc1OC]

(X)

which is converted, by a bromination reaction, into a compound of formula (VIII):

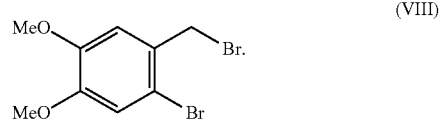 [SMILES: COc1cc(Br)c(CBr)cc1OC]

(VIII)

7. A process for the synthesis of ivabradine, or a pharmaceutically acceptable salt thereof, wherein a compound of formula (VIII)

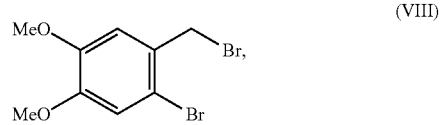 [SMILES: COc1cc(Br)c(CBr)cc1OC]

(VIII)

is subjected to the action of a base in the presence of acetonitrile in an organic solvent to yield a compound of formula (I):

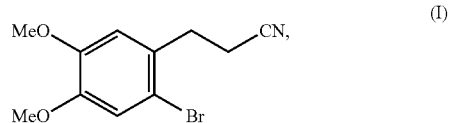 [SMILES: COc1cc(Br)c(CCC#N)cc1OC]

(I)

which compound of formula (I) is subjected to an intramolecular cyclization reaction in a basic medium to yield a compound of formula (III):

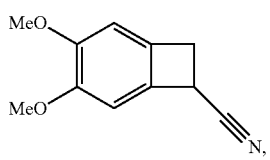

(III)

which compound of formula (III) is subjected to reduction conditions to yield a compound of formula (IV):

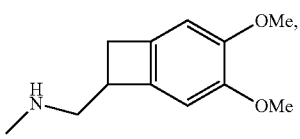

(IV)

which compound of formula (IV) is subjected to optical resolution conditions to yield a compound of formula (V):

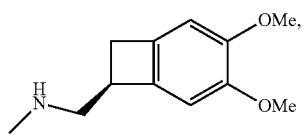

(V)

which compound of formula (V) is reacted with a compound of formula (VI):

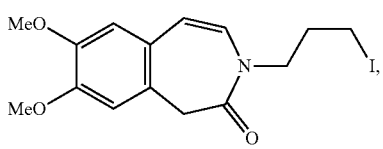

(VI)

to yield a compound of formula (VII):

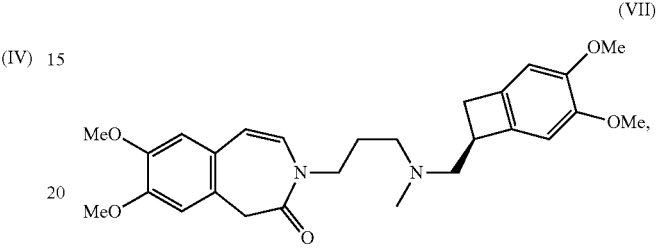

(VII)

which compound of formula (VII) is subjected to catalytic hydrogenation conditions to yield ivabradine, which may optionally be converted into an addition salt thereof via treatment with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

* * * * *